US00PP37811P2

(12) United States Plant Patent
Matsubara

(10) Patent No.: US PP37,811 P2
(45) Date of Patent: Oct. 20, 2026

(54) ***PETUNIA* PLANT NAMED 'Keipespapmom'**

(50) Latin Name: ***Petunia* x *hybrida***
Varietal Denomination: Keipespapmom

(71) Applicant: KEISEI ROSE NURSERIES INC., Yachiyo (JP)

(72) Inventor: Susumu Matsubara, Yachimata (JP)

(73) Assignee: REISEI ROSE NURSERIES INC., Yachiyo (JP)

( * ) Notice: Subject to any disclaimer, the term of this patent is extended or adjusted under 35 U.S.C. 154(b) by 0 days.

(21) Appl. No.: 19/650,856

(22) Filed: Apr. 17, 2026

(51) Int. Cl.
*A01H 5/02* (2018.01)

(52) U.S. Cl.
USPC ..... Plt./356.11

(58) Field of Classification Search
USPC ..... Plt./263.1, 356.1, 356.11
See application file for complete search history.

(56) References Cited

U.S. PATENT DOCUMENTS

PP26,888 P3 * 6/2016 Danziger ..... A01H 5/02
Plt./413

* cited by examiner

*Primary Examiner* — Karen M Redden
(74) *Attorney, Agent, or Firm* — C. Anne Whealy

(57) ABSTRACT

A new and distinct cultivar of *Petunia* plant named 'Keipespapmom', characterized by its semi-trailing plant habit; vigorous growth habit; freely branching habit; freely flowering habit; long and continuous flowering period; salmon pink-colored flowers with dark red-colored throats; and good garden performance.

2 Drawing Sheets

Figure 1:
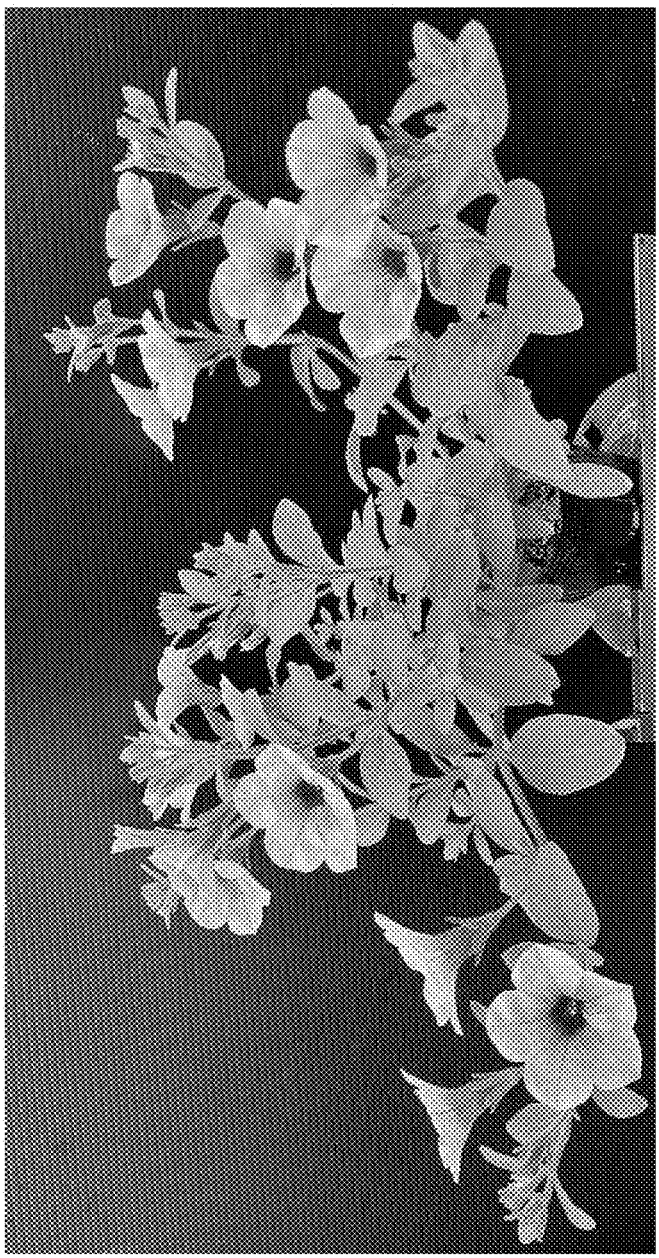

Botanical designation: *Petunia* x *hybrida*.
Cultivar denomination: 'KEIPESPAPMOM'.

CROSS-REFERENCED TO CLOSELY-RELATED APPLICATIONS

A Japanese Plant Breeder's Rights application for the instant plant was filed by the Applicant/Assignee, Keisei Rose Nurseries Inc. of Yachiyo, Chiba, Japan on Mar. 3, 2026, application number 38446. Foreign priority is not claimed to this application.

BACKGROUND OF THE INVENTION

The present invention relates to a new and distinct cultivar of *Petunia* plant, botanically known as *Petunia* x *hybrida* and hereinafter referred to by the name 'Keipespapmom'.

The new *Petunia* plant is a product of a planned breeding program conducted by the Inventor in Katori, Chiba, Japan. The objective of the breeding program is to create new trailing type and early-flowering *Petunia* plants with numerous attractive flowers.

The new *Petunia* plant originated from a cross-pollination made by the Inventor in October, 2019 in Katori, Chiba, Japan of an unnamed proprietary selection of *Petunia* x *hybrida*, not patented, as the female, or seed, parent with an unnamed proprietary selection of *Petunia* x *hybrida*, not patented, as the male, or pollen, parent. The new *Petunia* plant was discovered and selected by the Inventor as a single flowering plant within the progeny of the stated cross-pollination in a controlled greenhouse environment in Katori, Chiba, Japan in June, 2020.

Asexual reproduction of the new *Petunia* plant by terminal vegetative cuttings in a controlled greenhouse environment in Katori, Chiba, Japan since June, 2020 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Keipespapmom'. These characteristics in combination distinguish 'Keipespapmom' as a new and distinct *Petunia* plant:

1. Semi-trailing plant habit.
2. Vigorous growth habit.
3. Freely branching habit.
4. Freely flowering habit.
5. Long and continuous flowering period.
6. Salmon pink-colored flowers with dark red-colored throats.
7. Good garden performance.

Plants of the new *Petunia* can be compared to plants of the female parent selection. Plants of the new *Petunia* differ primarily from plants of the female parent selection in the following characteristics:

1. The plant habit of plants of the new *Petunia* is not as trailing as the plant habit of plants of the female parent selection.
2. Plants of the new *Petunia* are more freely flowering than plants of the female parent selection.

3. Plants of the new *Petunia* are salmon pink in color with dark red-colored throats whereas flowers of plants of the female parent selection are magenta in color.

Plants of the new *Petunia* can be compared to plants of the male parent selection. Plants of the new *Petunia* differ primarily from plants of the male parent selection in the following characteristics:

1. The plant habit of plants of the new *Petunia* is not as upright as the plant habit of plants of the male parent selection.
2. Plants of the new *Petunia* are more freely flowering than plants of the male parent selection.
3. Plants of the new *Petunia* are salmon pink in color with dark red-colored throats whereas flowers of plants of the male parent selection are yellow in color.

Plants of the new *Petunia* can also be compared to plants of the *Petunia sensu wijsman* 'DCAS303', disclosed in U.S. Plant Pat. No. 26,888. In side-by-side comparisons, plants of the new *Petunia* and 'DCAS303' differ primarily in the following characteristics:

1. Leaf apices of plants of the new *Petunia* are obtuse whereas leaf apices of plants of 'DCAS303' are acute.
2. Plants of the new *Petunia* have larger flowers than plants of 'DCAS303'.
3. Plants of the new *Petunia* and 'DCAS303' differ in flower color as flowers of plants of the new *Petunia* are salmon pink in color with dark red-colored throats whereas flowers of plants of 'DCAS303' are orange pink in color with greyish red-colored throats.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'Keipespapmom' grown in a container.

Figure 2:
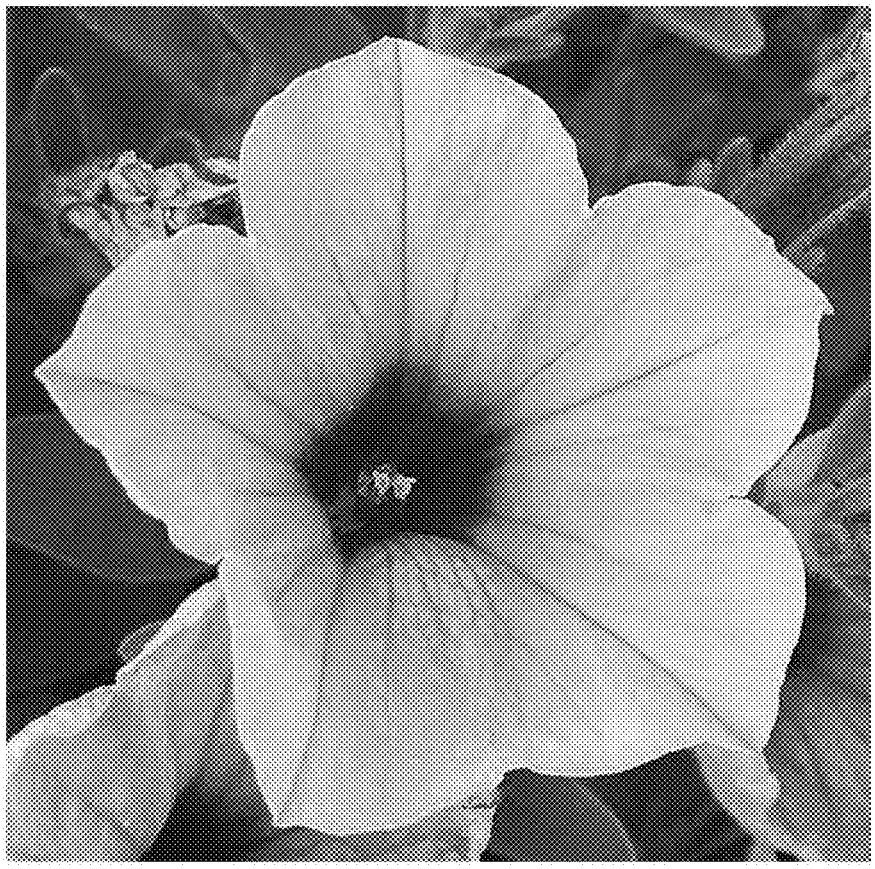

The photograph on the second sheet (FIG. 2) is a close-up view of a typical flower of 'Keipespapmom'.

DETAILED BOTANICAL DESCRIPTION

The aforementioned photographs and following observations, measurements and values describe plants grown during the spring in 9-cm containers in a glass-covered greenhouse in Katori, Chiba, Japan and under cultural practices typical of commercial *Petunia* production. During the production of the plants, day temperatures averaged 15° C. and night temperatures averaged 10° C. Plants were pinched one time and were four months old when the photographs and description were taken. In the following description, color references are made to The Royal Horticultural Society Colour Chart, 2007 Edition, except where general terms of ordinary dictionary significance are used.

Botanical classification: *Petunia* x *hybrida* 'Keipespapmom'.

Parentage:

*Female, or seed, parent*.—Unnamed proprietary selection of *Petunia* x *hybrida*, not patented.

*Male, or pollen, parent*.—Unnamed proprietary selection of *Petunia* x *hybrida*, not patented.

Propagation:

*Type*.—By terminal vegetative cuttings.

*Time to initiate roots, summer*.—About one week at temperatures about 25° C.

*Time to initiate roots, winter*.—About three weeks at temperatures about 10° C.

*Time to produce a rooted young plant, summer*.—About three weeks at temperatures about 25° C.

*Time to produce a rooted young plant, winter*.—About four weeks at temperatures about 20° C.

*Root description*.—Medium in thickness, fibrous; typically light brown to white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Semi-trailing plant habit; freely branching habit with numerous lateral branches developing per plant; pinching enhances lateral branch development; vigorous growth habit and moderate growth rate.

*Plant height*.—About 16 cm.

*Plant diameter*.—About 50 cm.

Lateral branch description:

*Length*.—About 30 cm.

*Diameter*.—About 3 mm.

*Internode length*.—About 1.2 cm.

*Strength*.—Strong, flexible.

*Texture*.—Pubescent.

*Color*.—Close to 143B.

Leaf description:

*Arrangement*.—Alternate, simple.

*Length*.—About 3 cm.

*Width*.—About 2.2 cm.

*Shape*.—Ovate.

*Apex*.—Obtuse.

*Base*.—Cuneate.

*Margin*.—Entire.

*Texture, upper and lower surfaces*.—Pubescent.

*Venation pattern*.—Pinnate.

*Color*.—Developing leaves, upper and lower surfaces: Close to 143A. Fully expanded leaves, upper surface: Close to 137A; venation, close to 143B. Fully expanded leaves, lower surface: Close to 137C; venation, close to 143B.

*Petioles*.—Length: About 2 mm. Diameter: About 1.5 mm. Texture, upper and lower surfaces: Pubescent. Color, upper surface: Close to 143A. Color, lower surface: Close to 143B.

Flower description:

*Flower arrangement and habit*.—Single salverform flowers arising from upper leaf axils; freely flowering habit with numerous flowers continuously developing during the flowering season; flowers face upright to outwardly.

*Fragrance*.—Faint; pleasant.

*Natural flowering season*.—Early flowering habit; plants of the new *Petunia* initiate and develop flowers about two to three weeks after planting; long flowering period, plants flower continuously from late March to late October in Japan.

*Flower longevity*.—Individual flowers last about five days on the plant.

*Flower buds*.—Length: About 3.5 cm. Diameter: About 6 mm. Shape: Cylindrical. Color: Close to 145A.

*Flower diameter*.—About 5.5 cm.

*Flower tube length*.—About 3.4 cm.

*Flower throat diameter*.—About 1.3 cm.

*Flower tube length*.—About 1.9 cm.

*Flower tube diameter, proximally*.—About 4 mm.

*Corolla*.—Quantity and arrangement: Five in a single whorl, fused at the base and opening into a flared trumpet with shallow lobes. Petal length from throat: About 2.5 cm. Petal width: About 2.7 cm. Petal shape: Spatulate. Petal apex: Obtuse to acute. Petal margin: Entire; slightly undulate. Petal texture, upper and lower surfaces: Smooth, glabrous. Throat texture: Smooth, glabrous. Tube texture: Smooth, glabrous. Color: Petal, when opening, upper surface: Close to 171D. Petal, when opening, lower surface: Close to 160B. Petal, fully opened, upper surface: Close to 180D; venation, close to 183B; color becoming closer to 184C with subsequent development. Petal, fully opened, lower surface: Close to 161C; venation, close to 183C. Throat: Close to 183D; venation, close to 184A. Tube: Close to 183A; venation, close to 183B.

*Calyx*.—Arrangement: One star-shaped calyx tube with five sepals arranged in a single whorl and fused at the base into a tube. Sepal length: About 1.7 cm. Sepal width: About 3 mm. Sepal shape: Narrowly elliptic; outwardly arching. Sepal apex: Obtuse. Sepal margin: Entire. Sepal texture, upper and lower surfaces: Pubescent. Color, upper surface: Close to 137C. Color, lower surface: Close to 137D.

*Peduncles*.—Length: About 4.4 cm. Diameter: About 2 mm. Strength: Moderately strong, flexible. Aspect: Upright to outwardly. Texture: Pubescent; viscid. Color: Close to 143C.

*Reproductive organs*.—Stamens: Quantity per flower: Five. Anther shape: Roughly round. Anther size: About 1 mm by 2 mm. Anther color: Close to 150C. Pollen amount: Moderate. Pollen color: Close to 150D. Pistils: Quantity per flower: One. Pistil length: About 1.4 cm. Style length: About 1.3 cm. Style color: Close to 141D. Stigma shape: Roughly round. Stigma color: Close to 141C. Ovary color: Close to 141D. Seeds and fruits: To date, seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: To date, plants of the new *Petunia* have not been observed to be resistant to pathogens and pests common to *Petunia* plants.

It is claimed:

1. A new and distinct *Petunia* plant named 'Keipespapmom' as herein illustrated and described.

* * * * *